United States Patent [19]

Sugawara et al.

[11] Patent Number: 5,332,574
[45] Date of Patent: Jul. 26, 1994

[54] COMPOUNDS PRODUCED BY A STRAIN OF STREPTOMYCES EXFOLIATUS

[75] Inventors: Koko Sugawara, Saitama; Koji Tomita, Tokyo, both of Japan; Michael R. Kozlowski, Noank, Conn.; Yosuke Sawada, Tokyo, Japan

[73] Assignee: Bristol-Myers Squibb Company, New York, N.Y.

[21] Appl. No.: 16,380

[22] Filed: Feb. 11, 1993

[51] Int. Cl.$^5$ .......................... A61K 35/74; C12P 1/06
[52] U.S. Cl. ..................................... 424/121; 435/169
[58] Field of Search ........................ 424/121; 435/169

[56] References Cited

PUBLICATIONS

Berge, S. M., et al., "Pharmaceutical Salts," *J. Pharm. Sci.,* (1977), 66(1), 1–19.
Noma, A., "ATP–Regulated K+Channels in Cardiac Muscle," *Nature,* (1983), 305, 147–148.
Sturgess, N. C., et al., "The Sulphonylurea Receptor May Be An ATP–Sensitive Potassium Channel," *The Lancet,* (1985), 8453, 474–475.
Spruce, et al., "Voltage-dependent ATP-sensitive Potassium Channels of Skeletal Muscle Membrane," *Nature* (1985), 316, 736–738.
Ashford, M. L. J., et al., "Adenosine-5'-triphosphate-sensitive Ion Channels in Neonatal Rat Cultured Central Neurons," *Pflugers Arch.* (1988), 412, 297–304.
Sturgess, N. C., et al. "Effects of Sulphonylureas and Diazoxide on Insulin Secretion and Nucleotide-sensitive Channels in an Insulin-secreting Cell Line," *Br. J. Pharmacol.,* (1988), 95, 83–94.
Fosset, M., et al., "Antidiabetic Sulfonylureas Control Action Potential Properties in Heart Cells via High Affinity Receptors That Are Linked to ATP-dependent K+Channels," *J. Biol. Chem.,* (1988), 263(17), 7933–7936.
Gaines, K. L., et al., "Characterization of the Sulfonylurea Receptor on Beta Cell Membranes," *J. Biol. Chem.,* (1988), 263(6), 2589–2592.
Geisen, K., et al., "Inhibition of $^3$H-Glibenclamide Binding to Sulfonylurea Receptors by Oral Antidiabetics," *Arznheimittel-Forsch,* (1985), 35, 707–712.
French, J. F., et al., "Identification of High and Low (GTP-Sensitive) Affinity [$^3$H]Glibenclamide Binding Sites in Cardiac Ventricular Membranes," *Biochem. Biophys. Res. Commun.,* (1990), 167(3), 1400–1405.
Williams, S. T. et al., In Bergey's Manual of Systematic Bacteriology, vol. 4, Williams & Wilkins, Baltimore, 1989, Section 29, "Genus Streptomyces Waksman and Henrici 1943, 339", pp. 2452–2492.
Lechevalier, M. P., "Identification of Aerobic Actinomycetes of Clinical Importance," *J. Lab. Clin. Med.,* (1968), 71, 934–944.
Collins, M. D., et al., "Distribution of Menaquinones in Actinomycetes and Corynebacteria," *J. Gen. Microbiol.* (1977), 100, 221–230.
Sugawara, K., et al., "Eponemycin, A New Antibiotic Active Against B16 Melanoma, I. Production, Isolation, Structure and Biological Activity," *J. Antibiotics,* (1990), 43(1), 8–18.
French, J. F., et al., "Modulation of [$^3$H]Glibenclamide Binding to Cardiac and Insulinoma Membranes," *Euro. J. Pharmacol.,* (1991), 207, 23–28.
Suemitsu, R., et al., "Alterporriol D and E, Modified Bianthraquinones From *Alternaria porri* Ciferri," *Agric. Biol. Chem.,* (1989), 53(5), 1301–1304.
Nelson, R. A., et al., "Crisamicin A, A New Antibiotic From Micromonospora I. Taxonomy of the Producing Strain, Fermentation, Isolation, Physico-chemical Characterization and Antimicrobial properties," *J. Antibiotics,* (1986), 39(3), 335–344.
Ling, D., et al., "Isolation and Structure Determination of Crisamicin A, A New Antibiotic From *Micromonospora purpureochromogenes* Subsp. Halotolerans," *J. Antibiotics,* (1986), 39(3), 345–353.
Shoji, Jun-Ichi, et al., "Julymycin B-II, A New Antibiotic, Isolation and Characterization," *J. Antibiotics, Ser. A,* (1964), 17(4), 156–160.

*Primary Examiner*—Jerome D. Goldberg
*Attorney, Agent, or Firm*—Thomas R. Savitsky

[57] ABSTRACT

Disclosed are active compounds BU-4726G-A and BU-4726G-B which contain a quinone chromophore and hydroquinone chromophore, respectively. The compounds are produced by fermentation of Streptomyces exfoliatus AA4510. The compounds possess antimicrobial, and $K_{ATP}$ channel blocking activities.

7 Claims, 7 Drawing Sheets

COMPOUNDS PRODUCED BY A STRAIN OF *STREPTOMYCES EXFOLIATUS*

FIELD OF THE INVENTION

The present invention concerns novel compounds, BU-4726G-A and BU-4726G-B, produced by *Streptomyces exfoliatus*.

SUMMARY OF THE INVENTION

The present invention is based on the discovery of a new microorganism strain which produces biologically active compounds. The compounds of the invention are referred to herein as compound "BU-4726G-A" and compound "BU-4726G-B", which terms also include pharmaceutically acceptable salts of the compounds. The term "BU-4726G" (without the "A" or "B" suffix) refers to a mixture of the two individual compounds. The present invention is also directed to pharmaceutical compositions comprising one or both of the compounds of the invention together with a pharmaceutically acceptable carrier.

Compounds BU-4726G-A and BU-4726G-B have been found to be produced by a microorganism, strain AA4510, identified as belonging to the species *Streptomyces exfoliatus*. Thus, the present invention is also directed to a biologically pure culture of *Streptomyces exfoliatus* AA4510. It is also contemplated that mutants and variants of *Streptomyces exfoliatus* AA4510 are also within the scope of the present invention, whether created by conventional physical or chemical means or by recombinant genetic engineering techniques. The present invention also includes a process for producing the compounds of the invention comprising cultivating under aerobic conditions *Streptomyces exfoliatus* AA4510 or a mutant or variant thereof in a suitable culture medium containing a carbon source and a nitrogen source at a pH and temperature and for a time sufficient for production of one or both of said compounds.

Additionally, the present invention is directed to a method for controlling bacteria which comprises applying to said bacteria or habitat thereof an effective amount of an active compound selected from the group consisting of compound BU-4726G-A, compound BU-4726G-B, and a mixture thereof.

Finally, the present invention is directed to a method for blocking the $K_{ATP}$ channel of a mammal comprising administering to said mammal an effective amount of an active compound selected from the group consisting of compound BU-4726G-A, compound BU-4726G-B, and a mixture thereof.

DETAILED DESCRIPTION OF THE INVENTION

Figure 1:
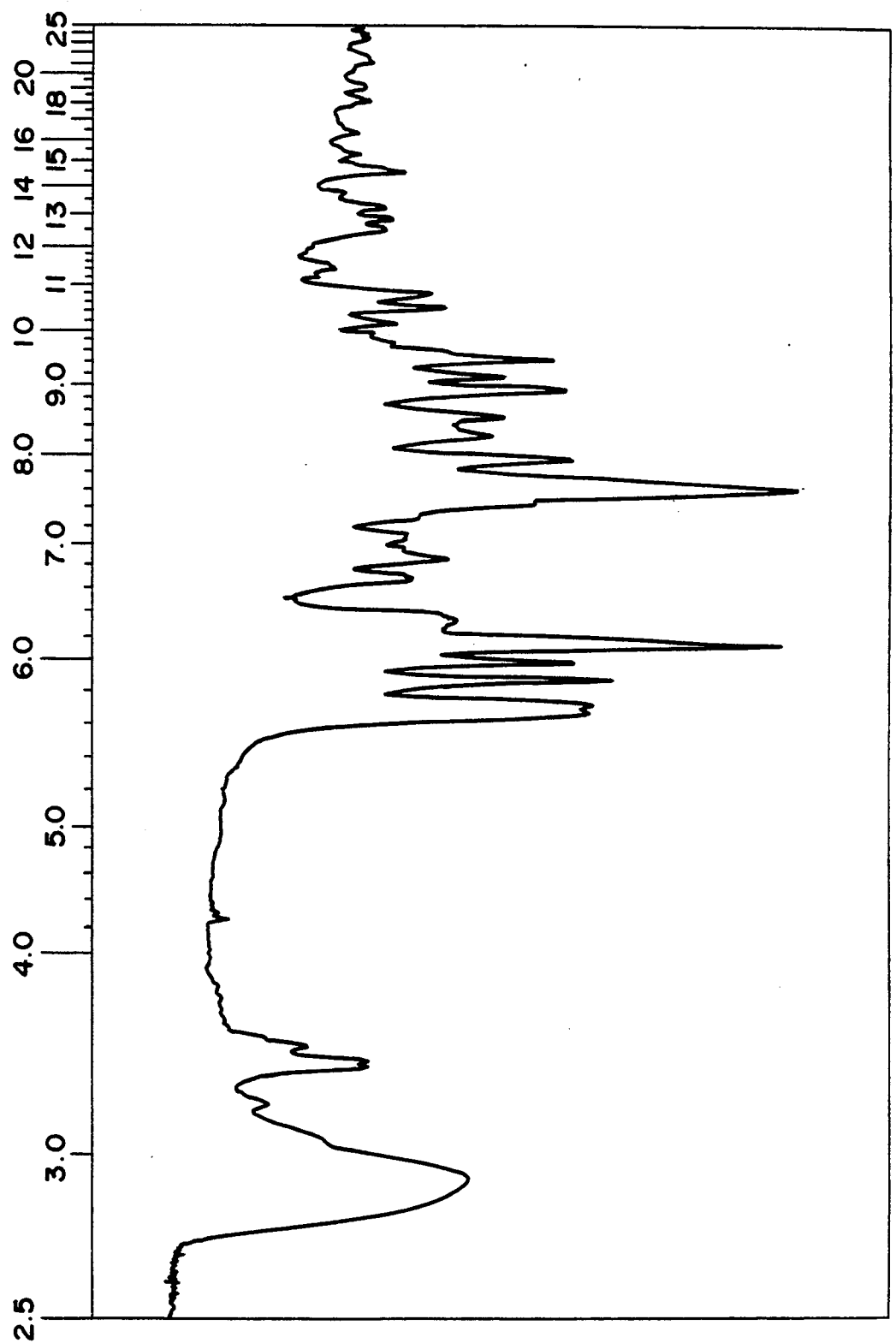
FIG. 1—Infrared (IR) spectrum of compound BU-4726G-A.
Figure 2:
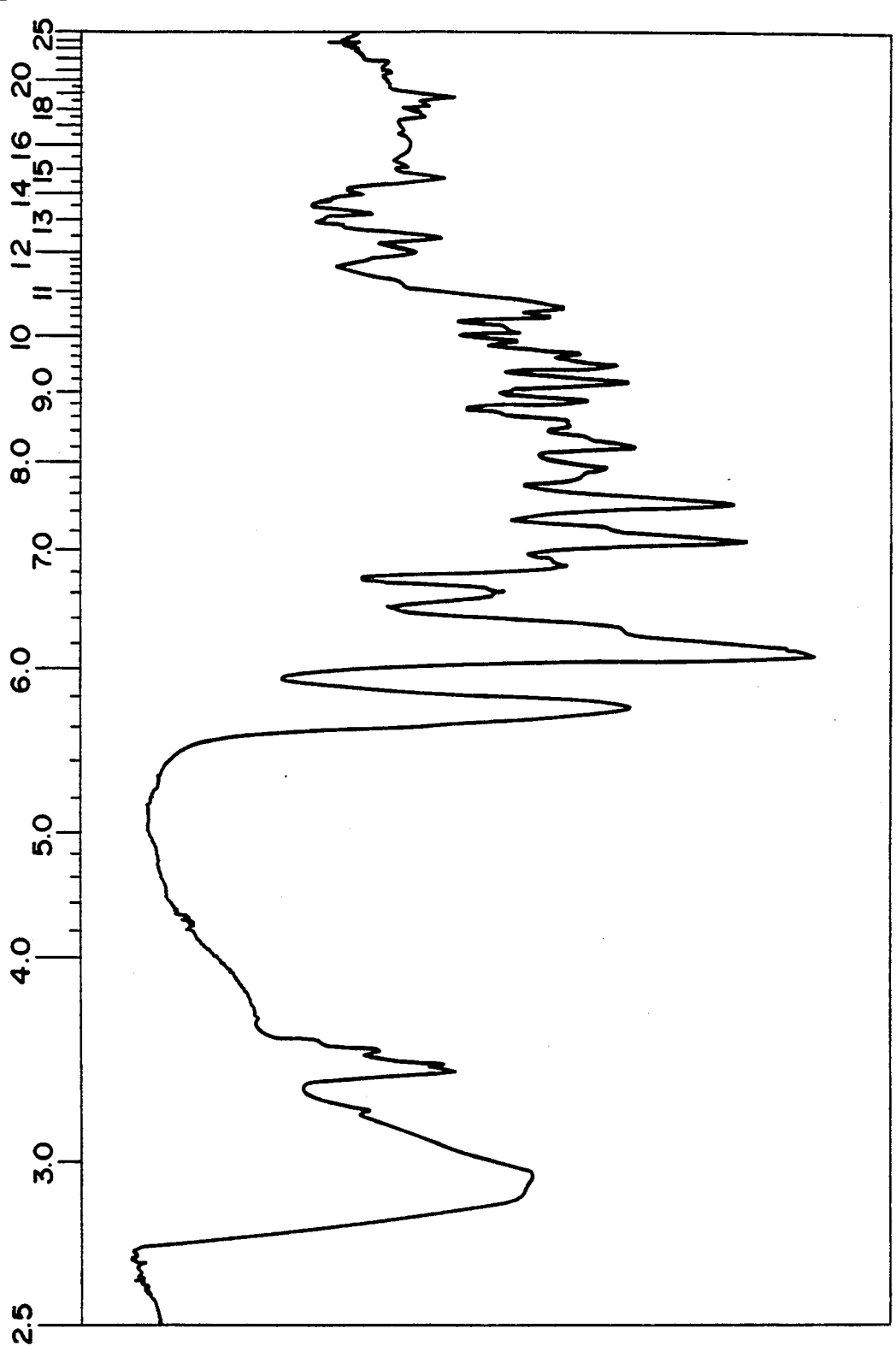
FIG. 2—IR spectrum of compound BU-4726G-B.
Figure 3:
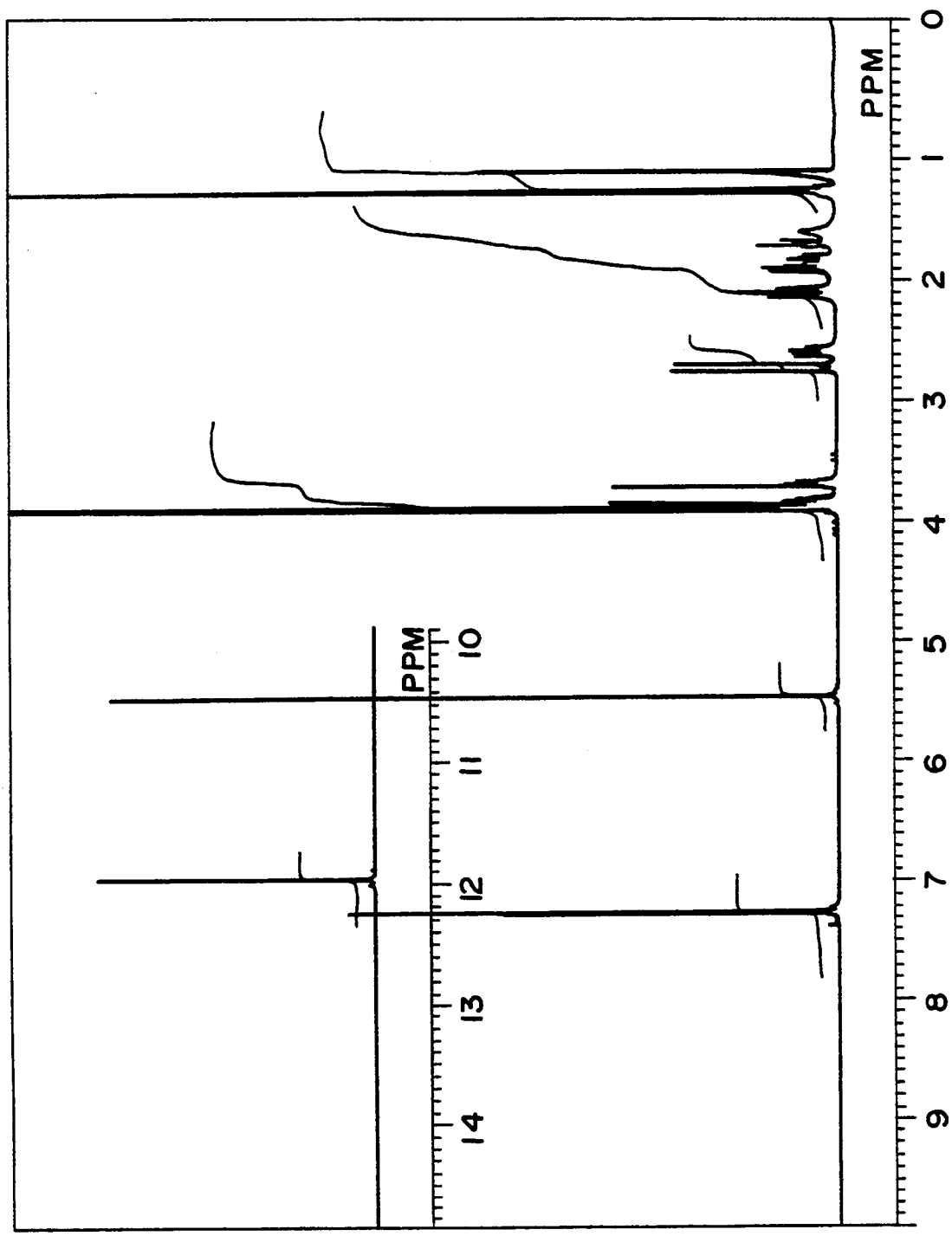
FIG. 3—Proton nuclear magnetic resonance ($^1$H-NMR) spectrum of compound BU-4726G-A (400 MHz in $CDCl_3$).
Figure 4:
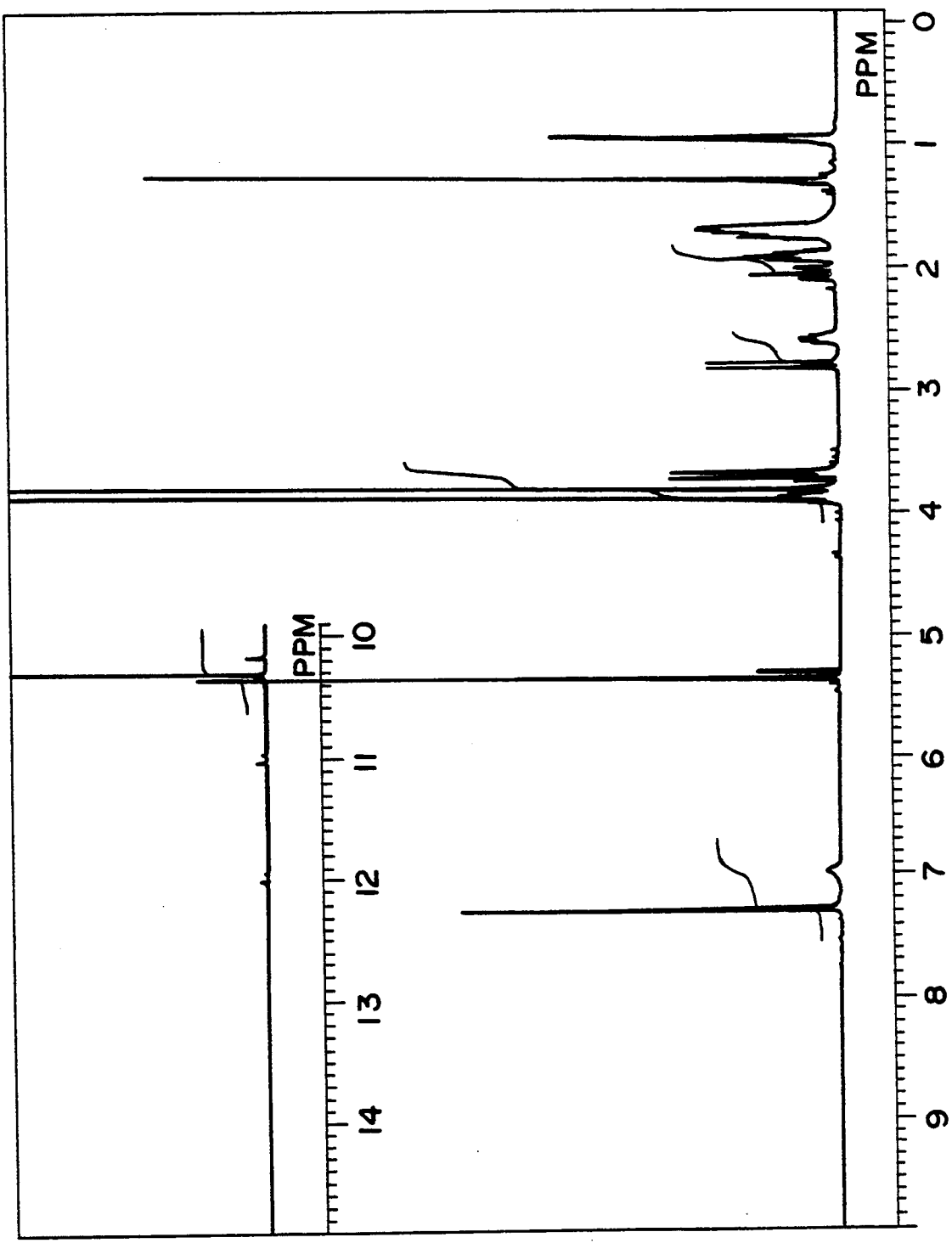
FIG. 4—$^1$H-NMR spectrum of compound BU-4726G-B (400 MHz in $CDCl_3$).
Figure 5:
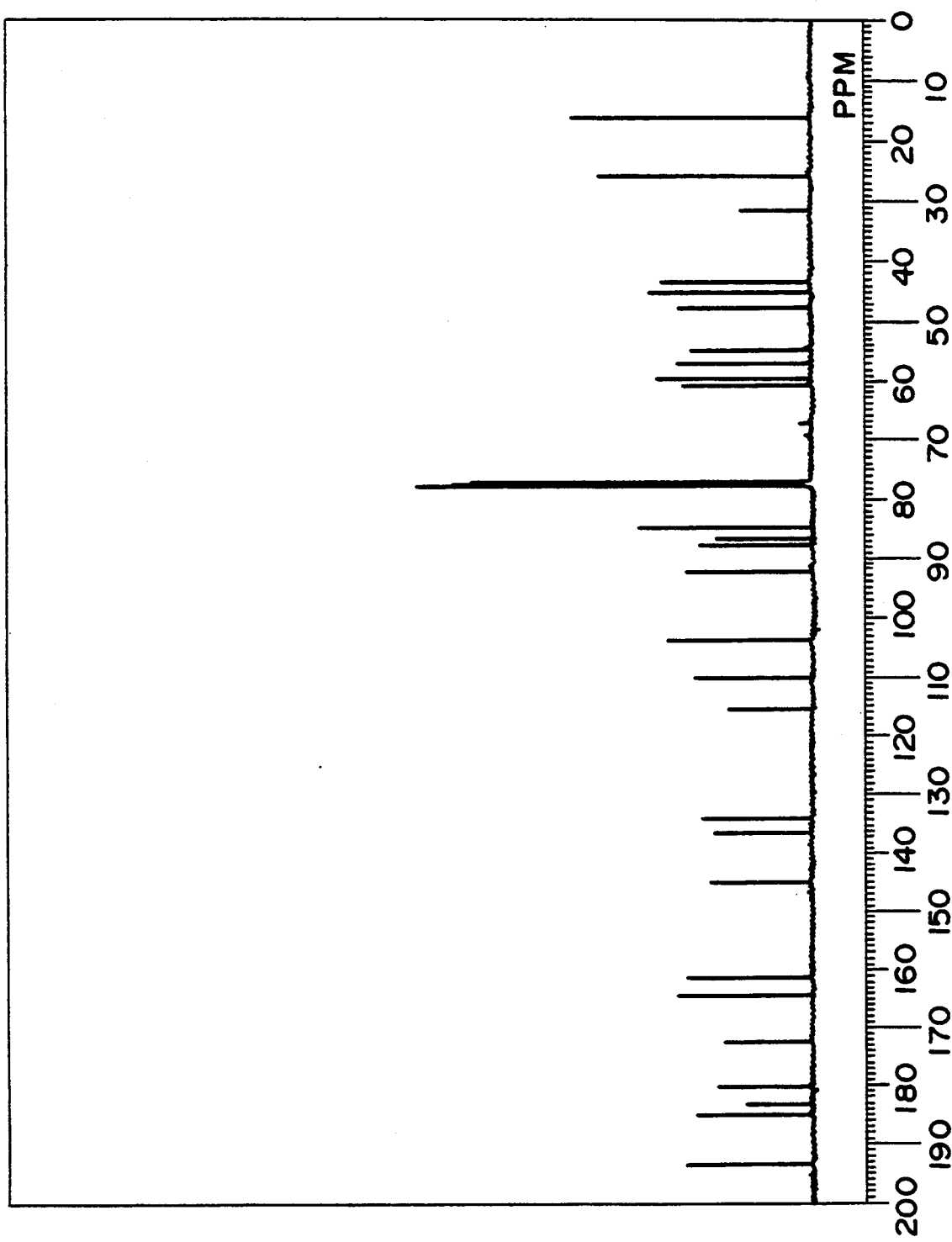
FIG. 5—$^{13}$C-NMR spectrum of compound BU-4726G-A (100 MHz in $CDCl_3$).
Figure 6:
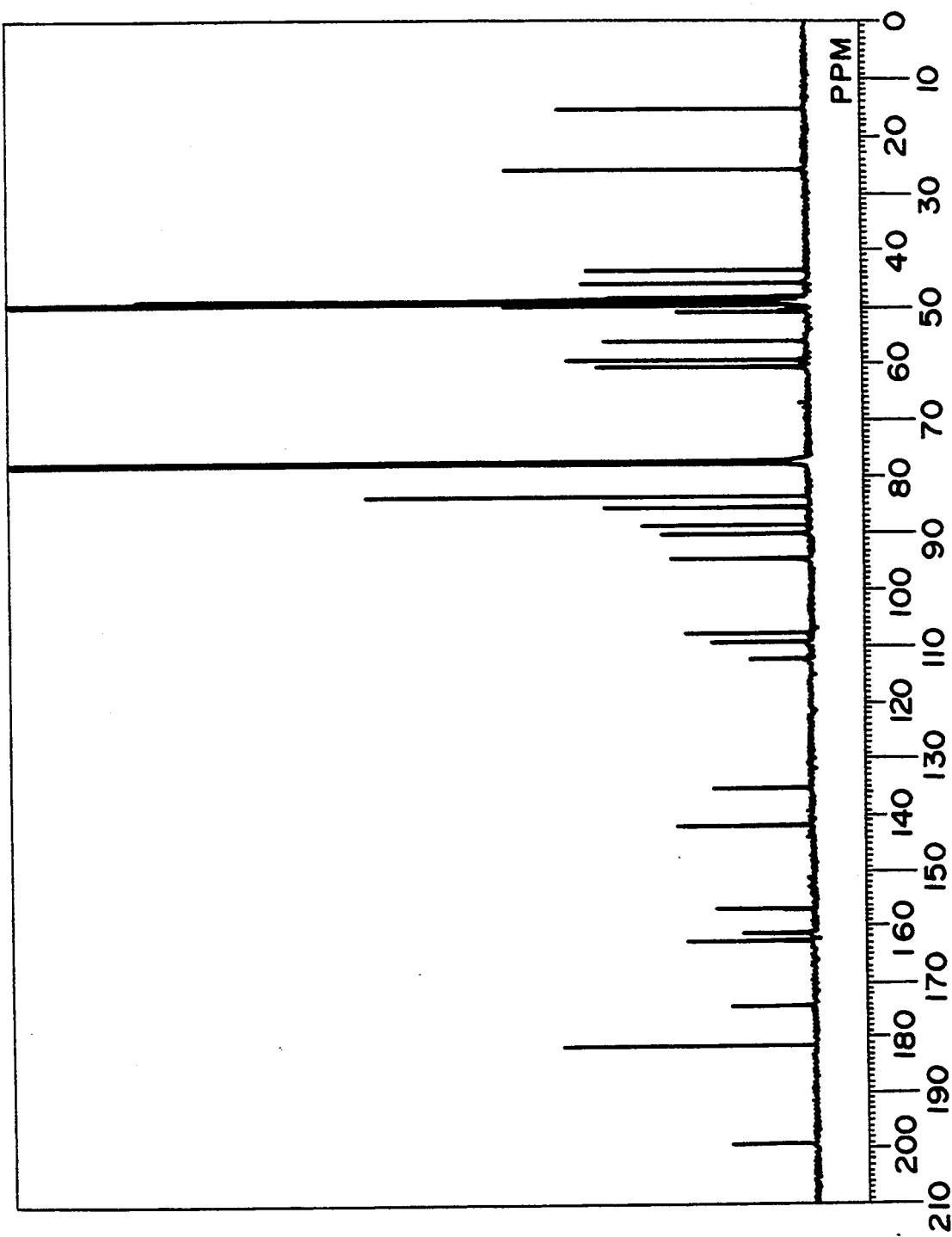
FIG. 6—$^{13}$C-NMR spectrum of compound BU-4726G-B (100 MHz in $CDCl_3 + CD_3OD$).

An actinomycete, strain AA4510, which produces novel biologically active compounds, BU-4726G-A and BU-4726G-B, was isolated from a soil sample collected in Uttar Pradesh State, India. Based on the morphological, cultural and physiological characteristics and cell chemistry, strain AA4510 was identified as *Streptomyces exfoliatus*. This organism has been deposited with the American Type Culture Collection (ATCC) under the Accession Number ATCC-55317.

It is to be understood that the present invention is not limited to use of the particular strain AA4510 or to organisms fully answering the description contained herein. It is especially intended to include other BU-4726G-A or BU-4726G-B producing strains or mutants or variants of said organisms which can be produced from the described organism by known means such as X-ray irradiation, ultraviolet irradiation, treatment with nitrogen mustard, phage exposure, and the like; or through the use of recombinant genetic engineering techniques.

The compounds of the present invention are produced by cultivating *Streptomyces exfoliatus* AA4510, or a mutant or a variant thereof, in a conventional aqueous medium. The organism is grown in a nutrient medium containing known nutritional sources for acetinomycetes, i.e. assimilable sources of carbon and nitrogen plus optional inorganic salts and other known growth factors. Submerged aerobic conditions are preferably employed for the production of large quantities of active compounds, although for production of limited amounts, surface cultures and bottles may also be used. The general procedures used for the cultivation of other actinomycetes are applicable to the present invention. The nutrient medium should contain an appropriate assimilable carbon source such as sucrose, starch, glucose, xylose, mannitol, fructose, glycerol, L-arabinose, galactose, mannose, lactose, cellobiose, melibiose, trehalose, or raffinose. As nitrogen sources, ammonium chloride, ammonium sulfate, urea, ammonium nitrate, sodium nitrate, etc. may be used or organic nitrogen sources such as peptone, fish meat extract or fish meal, yeast extract, meat extract such as beef extract, corn steep liquor, soybean powder, NZ-case, cotton seed flour, etc., may be used, or any combination thereof. There may also be added if necessary nutrient inorganic salts to provide sources of sodium, potassium, calcium, ammonium, phosphate, sulfate, chloride, bromide, carbonate, zinc, magnesium, manganese, cobalt, iron and the like. Ordinarily, optimum production of the compounds of the invention is obtained in shake flasks after an appropriate incubation period. Aeration in shake flasks is achieved by agitation, e.g. shaking on a rotary shaker. If fermentation is to be carried out in tank fermentors, it is desirable to produce a vegetative inoculum in a nutrient broth by inoculating the broth culture from a slant culture of a lyophilized culture of the organism or with vegetative mycelia stored at a low temperature (e.g. $-80°$ C.) in the presence of glycerol. After obtaining an active inoculum in this manner, it is aseptically transferred to the fermentation tank medium. Agitation in the tank fermentor is provided by stirring and aeration may be achieved by injection of air or oxygen into the agitated mixture. Production of BU- 4726G-A and/or BU-4726G-B may be monitored using chromatographic or spectroscopic techniques, or by a conventional biological assay.

Preferred culture conditions include a pH of about 6 to about 8 and temperature of about 16° C. to about 48° C., and an incubation period of about 2 days to about 10 days. More preferred conditions include a pH of about 7, a temperature of about 31° C. to about 37° C., and an incubation period of about 3 days to about 5 days.

After cultivation and production of the active compounds, said compounds can be isolated by techniques known in the art and/or taught herein. For example, the fermented whole broth can be extracted by contact with a suitable organic solvent such as n-butanol, n-butyl acetate or 4-methyl-2-pentanone, preferably under agitation. The organic layer can then be separated, e.g. by centrifugation 10 followed by removal of the solvent, e.g. by evaporation to dryness, preferably under vacuum. The resulting residue can then optionally be reconstituted (e.g. in a water ethyl acetate mixture) and re-extracted with a suitable organic solvent such as hexane. After removal of solvent, the active compound can be further purified/isolated by use of standard techniques such as chromatography, particularly column chromatography, optionally followed by further purification, e.g. by use of reverse phase chromatography. Various modifications to any particular isolation/purification procedure will be apparent to a skilled artisan, but the final sample should show a single peak in a high performance liquid chromatography (HPLC) analysis.

For medicinal use, the pharmaceutically acceptable acid addition salts, those salts in which the anion does not contribute significantly to toxicity or pharmacological activity of their organic cation, are preferred. The acid addition salts are obtained either by reaction of one or both active compounds with an organic or inorganic acid, preferably by contact in solution, or by any of the standard methods detailed in the literature and available to a practitioner skilled in the art. Pharmaceutically acceptable salts of the compounds of the invention are illustratively hydrochloric, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methane and ethanesulfonic, hydroxymethane- and hydroxyethanesulfonic. (See, for example, "Pharmaceutical Salts," *J. Pharm. Sci.* 66(1):1-19 (1977)).

Compounds BU-4726G-A and BU-4726G-B have been found to be able to control microorganisms, particularly gram positive bacteria. The term "control" refers to antimicrobial activity such as the suppression, inhibition, kill, stasis, or destruction of microorganisms, or any interference with the growth of microorganisms which results in a slower growth rate. The term "effective amount" when used in conjunction with the antimicrobial method of the present invention refers to that amount of the compounds sufficient to result in control of microorganisms. The compounds of the invention are particularly effective against the genera Staphylococcus, Streptococcus, Micrococcus, Bacillus, and the like.

Compounds BU-4726G-A and BU-4726G-B can be used in a wide variety of applications in which control of microorganisms is desired. The compound is active against pathogenic and non-pathogenic bacteria which may be resistant to widely used known antibiotics. Because of this activity, the compounds can be used as therapeutic agents and administered to a patient in need of antibacterial treatment either orally, parenterally, or topically. As used herein, the term "treatment" whether used in conjunction with the antibacterial method or other methods, refers to amelioration, cure, or prevention of the appropriate disease, condition or infection.

One or both of the compounds of the invention or combinations containing the same can also be used as disinfectants, for example, to disinfect objects and instruments. The compound can be used as an antibacterial agent, for example, by contacting bacteria pests or their habitat with effective amounts sufficient to obtain control of many organisms. The compounds of this invention can be incorporated into various products susceptible to microbial degradation in order to prevent such degradation of the products by the microorganisms.

The compounds of the invention possess ATP-sensitive $K^+$ ($K_{ATP}$) channel blocking activity. The ATP-sensitive $K^+$ channel was initially discovered in cardiac muscle (Noma, "ATP-regulated $K^+$ Channels in Cardiac Muscle, *Nature* (1983) 305, 147). Since then the channel has also been characterized in pancreatic B-cells (Sturgess, et al., "The Sulfonylurea Receptor May Be An ATP-sensitive Potassium Channel," *Lancet* (1985) 8453, 474), skeletal muscle (Spruce, et al., "Voltage-dependent ATP-sensitive Potassium Channels of Skeletal Muscle Membrane," *Nature* (1985) 316, 736) and cortical neurons (Ashford, et al., "Adenosine-5'-triphosphate-sensitive Ion Channels in Neonatal Rat Cultured central Neurons," *Pflugers Arch.* (1988) 412, 297). These channels play a role in regulation of insulin secretion from pancreatic B-cells (Sturgess, et al., "Effects of Sulfonylureas and Diazoxide on Insulin Secretion and Nucleotide-sensitive Channels in an Insulin-secreting Cell Line," *Brit. J. Pharmacol.* (1988) 95, 83) and in control of the action potential duration of anoxic cardiac tissue (Fosset, et al., "Antidiabetic Sulfonylureas Control Action Potential Properties in Heart Cells Via High Affinity Receptors That Are Linked to ATP-dependent $K^+$ Channels," *J. Biol. Chem.* (1988) 263, 7933). The channels are normally closed at physiological intracellular concentrations of ATP and open when the concentration decreases In pancreatic B-cells, the extracellular concentration of glucose is generally associated with the intracellular ATP level.

Glibenclamide (glyburide) is one of the sulfonylureas, hypoglycemic agents, which potently blocks the ATP-sensitive $K_{ATP}$ channel, resulting in B-cell membrane depolarization, increased $Ca^{++}$ influx and insulin secretion. Glybenclamide binding sites have been identified in pancreatic B-cells (Gaines, et al., "Characterization of the Sulfonylurea Receptor on Beta Cell Membranes," *J. Biol. Chem.* (1988), 263 2589; Geisen, et al., "Inhibition of $^3$H-glibenclamide Binding to Sulfonylurea Receptors by Oral Antidiabetics," *Arznheimittel-Forsch* (1985) 35, 707) and heart membranes (French, et al., "Identification of High and Low (GTP-sensitive) Affinity $^3$H-glibenclamide Binding Sites in Cardiac Ventricular Membranes," *Biochem. Biophys. Res. Commun.* (1990) 167, 1400). Therefore, a useful assay to discover new glibenclamide-mimetic compounds (either antagonists or agonists) involves searching for $^3$H-glibenclamide binding inhibitors using rat insulinoma cells which possess a glibenclamide binding receptor. Compounds BU-4726G-A and BU-4726G-B possess $K_{ATP}$ channel blocking activity as determined by use of the above-noted assay. Thus, it is expected that compounds BU-4726G-A and BU-4726G-B are not only useful as hypoglycemic agents but also are useful anti-arrhythmia agents and anti-ischemia agents in heart and brain, respectively. The term "blocking the $K_{ATP}$ channel" refers to reducing the level of cellular potassium ion efflux. Preferably, the $K_{ATP}$ channel blocking method is performed in humans. The term "effective amount" when used in conjunction with the $K_{ATP}$ channel blocking method of the invention refers to that amount of the compound(s) sufficient to result in blocking of the $K_{ATP}$ channel of mammals, especially humans.

The $K_{ATP}$ channel blocking method of this invention is intended to be a generic method which includes the hypoglycemia (anti-hyperglycemia) method, the anti-arrhythmia method, and the anti-ischemia method. Thus, the present invention is also directed to a method for preventing cell death in the brain due to ischemia in a mammal, especially a human, comprising administering to said mammal an effective amount of one or both compounds of the invention.

The present invention is also directed to a method for treatment of cardiovascular arrhythmia in a mammal, especially a human, comprising administering to said mammal an effective amount of one or both compounds of the invention.

Moreover, the present invention is directed to a method for treatment of hyperglycemia in a mammal, especially a human, comprising administering to said mammal an effective amount of one or both compounds of the invention.

The term "effective amount" when used in conjunction with the anti-ischemia, anti-arrhythmia, or hypoglycemia method of the invention refers to that amount of the compound(s) sufficient to result in the desired effect or treatment. Typically, this amount will be a therapeutic amount.

For the antibacterial method of the invention, a typical effective unit dose of the compounds given orally or parenterally would be from about 4 to about 40 milligram per kilogram (mg/kg) of body weight of the patient with a daily dose ranging from about 20 to about 200 mg/kg of body weight of the patient.

For the $K_{ATP}$ channel blocking method of the invention (including the anti-ischemia, anti-arrhythmia, and hypoglycemia methods), a typical effective unit dose of the compounds given orally or parenterally would be from about 3 to about 30 mg/kg of body weight of the patient with a daily dose ranging from about 15 to about 150 mg/kg of body weight of the patient.

For preparing pharmaceutical compositions from the compound(s) of this invention, inert, pharmaceutically acceptable carriers can be either solid or liquid. Solid form preparations include powders, tablets, dispersible granules, capsules, cachets, and suppositories.

In the pharmaceutical compositions of the invention the amount of active compound(s) of the invention is typically about 25 to about 100 weight percent of the total composition, preferably about 50 to about 100 weight percent.

A solid carrier can be one or more substances which may also act is diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound(s) is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool solidly.

Powders and tablets preferably contain between about 5% to about 50% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

For topical administration, the compound(s) may be incorporated into lotions, ointments, gels, creams, salves, tinctures, and the like.

Tablets, powders, cachets, and capsules can be used as solid dosage forms suitable for oral administration.

Liquid form preparations include solutions suitable for oral or parenteral administration; suspensions, or emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions for injection or infusion may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound(s) in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules and powders in vials or ampoules. The unit dosage form can also be capsule, cachet, or tablet itself, or it can be the appropriate number of any of these packaged forms.

The following examples are to illustrate the invention but should not be interpreted as a limitation thereon. All percentages are by weight unless otherwise indicated.

EXAMPLE 1

Taxonomy

Morphology of *S. exfoliatus* AA4510

The substrate mycelium was well-branched and non-fragmentary. Spore chains were formed on the monopodially branched aerial mycelium which was long and straight (30 or more spores per chain). The spores were short-cylindrical (0.5–0.7×0.8–1.3 micrometer (μm)) with smooth surface.

Cultural Characteristics of S. exfoliatus AA4510

Aerial mycelia only formed on yeast extract-malt extract agar, oatmeal agar and inorganic salts-starch agar so far tested were white; upon prolonged incubation the color faintly turned to pinkish gray or gray. Melanoid pigments were produced, but other distinct pigments were not. A summary of the cultural characteristics of S. exfoliatus AA4510 is contained in Table 1.

TABLE 1
Cultural Characteristics of Strain AA4510

| Medium | Growth | Aerial mycelium | Substrate mycelium | Diffusible pigment |
|---|---|---|---|---|
| Sucrose nitrate agar | Moderate | None | Deep yellow (85) | Grayish yellow (90) |
| Tryptone-yeast extract broth (ISP-1) | Poor; not turbid | None | Colorless | Dark brown (59) |
| Yeast extract-malt extract agar (ISP-2) | Good | Poor; white to pinkish gray (10) | Dark yellow (88) to dark brown (59) | Yellowish brown (74) |
| Oatmeal agar (ISP-3) | Moderate | Poor; white to grayish white | Light olive brown (94) | Grayish yellow (90) |
| Inorganic salts-starch agar (ISP-4) | Moderate | moderate; white to pinkish gray (10) | Dark yellow (88) | Grayish yellow (90) |
| Glycerol asparagine agar (ISP-5) | Poor | None | Grayish yellow (90) | None |
| Peptone-yeast extract-iron agar (ISP-6) | Poor | None | Colorless | Light brown (57) |
| Tyrosine agar (ISP-7) | Poor | None | Grayish olive (110) | Olive black (114) |
| Glucose asparagine agar | Scant | None | Pale yellow (89) | Yellowish white (92) |
| Bennett's agar | Poor | None | Moderate yellow (87) | Pale yellow (89) |

Observation after incubation at 28° C. for 3 weeks.
Color names and numerical codes used: ISCC-NBS Color-Name Charts.

Physiological and Biochemical Characteristics of S. exfoliatus AA4510

Gelatin and starch were hydrolyzed. Skimmed milk (10%, weight/volume (w/v)) was peptonized but not coagulated. Tyrosinase was produced. NaCl tolerance was seen at 5% but not at 7%. It was sensitive to lysozyme (0.01%, w/v). The temperature range of growth was between 16° and 48° C., and the optimal temperature at 33° C. (31° to 37° C.). No growth was seen at 13° C. and 53° C.

The utilization of carbohydrates and the physiological and biochemical characteristics according to the method described by Williams et al. (S. T. Williams, M. Goodfellow and G. Alderson, In Bergey's Manual of Systematic Bacteriology. Vol. 4, Genus Streptomyces Waksman and Henrici 1943, pp. 2452–2492. [eds. S. T. Williams, M. E. Sharpe and J. G. Holt], Williams and Wilkins Co., Baltimore, 1989) are shown in Tables 2 and 3, respectively.

TABLE 2
Carbohydrate Utilization of Strain AA4510

| Glycerol | + | Cellobiose | + |
|---|---|---|---|
| D-Arabinose | − | Melibiose | + |
| L-Arabinose | + | Trehalose | + |
| D-Xylose | + | Raffinose | + |
| D-Ribose | − | D-Melezitose | − |
| L-Rhamnose | − | Soluble starch | + |
| D-Glucose | + | Cellulose | − |
| D-Galactose | + | Dulcitol | − |
| D-Fructose | + | Inositol | − |
| D-Mannose | + | D-Mannitol | − |
| L-Sorbose | − | D-Sorbitol | − |
| Sucrose | + | Salicin | − |
| Lactose | + | | |

Basal medium: Pridham-Gottlieb's inorganic salts medium medium (ISP medium No. 9).
Observation after incubation at 28° C. for 2 weeks.
Symbols: +, used carbohydrate source;
−, did not use carbohydrate source.

TABLE 3
Physiological and Biochemical Characteristics of Strain AA4510

| Antibiosis against: | | sodium azide (0.01) | − |
|---|---|---|---|
| Bacillus Subtilis NCIB 3610 | + | Phenol (0.1) | + |
| Micrococcus luteus NCIB 196 | + | Potassium tellurite (0.001) | + |
| Candida albicans CBS 562 | − | Thallous acetate (0.001) | − |
| Saccharomyces cerevisiae CBS 1171 | − | Utilization of: | |
| Lecithinase activity | + | DL-α-Amino-n-butyrate | − |
| Lipolysis | + | L-cysteine | + |
| Nitrate reduction | + | L-Valine | − |
| H₂S production | + | L-Phenylalanine | + |
| Hippurate hydrolysis | + | L-Histidine | − |
| Degradation of: | | L-Hydroxyproline | + |
| Elastin | + | Sucrose | + |
| Xanthine | + | Meso-Inositol | − |
| Arbutin | + | Mannitol | − |
| | | L-Rhamnose | − |
| Resistance to: | | Raffinose | + |
| Neomycin (50 μg/ml) | − | D-Melezitose | − |
| Rifampicin (50 μg/ml) | − | Adonitol | − |
| Oleandomycin (100 μg/ml) | + | D-Melibiose | + |
| Penicillin G (10 i.u.) | + | Dextran | − |
| | | Xylitol | − |
| Growth at 45° C. | + | | |
| Growth with (%, w/v): NaCl (7.0) | − | | |

Symbols: +, positive: −, negative; i.u., international units.

Cell Chemistry of S. exfoliatus AA4510

Amino acid and sugar in the whole cell hydrolysate were analyzed by the method of Lechevalier (M.P. Lechevalier, "Identification of Aerobic Actinomycetes of Clinical Importance", J. Lab. Clin. Med., (1968) 71, 934–944). The menaquinones were prepared by the procedure of Collins et al. (M.D. Collins, T. Pirouz and M. Goodfellow, "Distribution of Menaquinones in Actinomycetes and Corynebacteria", *J. Gen. Microbiol.*, (1977) 100, 221–230) and analyzed by a mass spectrometry. The whole cell hydrolysate contained LL-diaminopimelic acid and none of diagnostic sugars. The major menaquinones were MK-9($H_6$), MK-9($H_8$), MK-9($H_4$), MK-8($H_6$), and MK-8($H_8$) (Table 4).

TABLE 4

Manaquinone Composition of Strain AA4510 and Two Other Species of Streptomyces

| | Menaquinone composition (%) | | | | | | | | | | |
|---|---|---|---|---|---|---|---|---|---|---|---|
| | MK-8 | | | | MK-9 | | | | | MK-10 | |
| Strain | $H_4$ | $H_6$ | $H_8$ | $H_{10}$ | $H_2$ | $H_4$ | $H_6$ | $H_8$ | $H_{10}$ | $H_4$ | $H_6$ |
| Strain AA4510 | 7 | 10 | 10 | 2 | 9 | 18 | 21 | 19 | 4 | | |
| *S. lavendulae* IAM 0009[T] | | 4 | | | 5 | 10 | 44 | 22 | 4 | 7 | 4 |
| *S. exfoliatus* NRRL 1237[T] | | 4 | 5 | | | 7 | 30 | 49 | 5 | | |

Taxonomic Position

The above-mentioned characteristics of strain AA4510 demonstrated that the strain was classified in the genus Streptomyces (Waksman and Henrici 1943). The strain had the following characteristics: Spore chains are Rectiflexibiles. The spore surface is smooth. The aerial mass color is red or gray. The reverse color is yellow to yellowish brown. Melanin pigment is produced. It is sensitive to NaCl at 7%, and grows at 45° C. Lecithinase and lipase are produced. L-Rhamnose, adonitol, inositol and D-mannitol are not utilized.

According to the descriptions of Williams et al., strain AA4510 was related to *Streptomyces exfoliatus* and *Streptomyces lavendulae*. The direct comparisons of strain AA4510 to the type strains of both species revealed that the strain was more related to *S. exfoliatus* than *S. lavendulae* in the cultural, physiological and biochemical characteristics and the menaquinone composition. Thus, strain AA4510 was identified as *Streptomyces exfoliatus*.

EXAMPLE 2

Production Of BU-4726G

Stocked Culture

Strain AA4510 was propagated at 28° C. for 7 days on Bn-3 agar slant composed of soluble starch (Nichiden Kagaku Co.) 0.5%, glucose 0.5%, meat extract (Mikuni Kagaku Kogyo Co.) 0.1%, yeast extract (Oriento Yeast Co.) 0.1%, NZ-case (Humko Sheffield Chemical Co.) 0.2%, NaCl 0.2%, $CaCO_3$ 0.1% and agar (Junsei Chemical Co.) 1.8%. A portion of the well-sporulated aerial mass on agar slant was inoculated into a seed medium in 500-ml Erlenmeyer flask and incubated for 4 days at 28° C. with 200 rpm on a rotary shaker. The seed medium composed of soluble starch 2%, glucose 0.5%, NZ-case 0.3%, yeast extract 0.2%, fish meal D30X (Banyu Nutrient Co.) 0.5% and $CaCO_3$ 0.3%. The resulting vegetative mycelia were spun down gently (3000 revolutions per minute (rpm) for 14 minutes at 4° C.) and resuspended with a half volume of 20% aqueous glycerol solution and stocked at −80° C.

Seed Culture

A portion (0.3 milliliter (ml)) of vegetative mycelia as set forth above was inoculated into 100 ml of seed medium in a 500-ml Erlenmeyer flask and incubated for 54 hours at the same conditions mentioned above.

Flask Fermentation

A 5 ml of the above seed culture was transferred into 500-ml Erlenmeyer flasks containing each 100 ml of a production medium FR-167A and incubated for 112 hours under the same conditions as those in the seed culture. The production medium FR-167A consisted of glucose 0.5%, glycerol 2%, soluble starch 2%, corn-steep liquor (Oji Corn Starch Co.) 1%, Pharmamedia (Trador's Co.) 1.5%, Ebios (Asahi Breweries, Ltd.) 0.2% and $CaCO_3$ 0.3%. The pH of medium was adjusted to 7.0 before autoclaving. The antibiotic activity in the fermentation broth was determined by a paper disc assay using *B. subtilis* PCI 219. BU-4726G production was reached at approximately 180 microgram (μg)/ml.

EXAMPLE 3

Isolation and Purification of Compound BU-4726G-A and Compound BU-4726G-B

The fermentation broth (9 liters (L), pH 7.0) obtained from flask fermentation by incubating for 112 hours was adjusted to pH 3.0 with 6N HCl and stirred with n-butyl alcohol (n-BuOH) (5 L) for one hour. The solvent layer was separated by centrifugation and concentrated under reduced pressure. The residue (7.3 grams (g)) was suspended in water (500 ml) and extracted three times with 500 ml each of ethyl acetate (EtOAc). The combined solvent extracts were evaporated in vacuo to yield an oil which was added dropwise into n-Hexane (1 L). The crude solid (2.97 g) precipitated was collected and charged on a column of silica gel (3.5 inside diameter (id)×50 centimeters (cm)) which was developed with methylene chloride-methyl alcohol (MeOH) mixture (100:0−9:1). The eluate were monitored by paper disk assay using *B. subtilis* PCI 219 and inhibitory activity against glybride binding. The first active fractions eluted with 4% methanol were pooled and concentrated in vacuo to yield a solid (1.6 g) which was further chromatographed on silica gel with EtOAc-MeOH (100:0−50:1) elution to afford a homogeneous solid of BU-4726G-A as an orange powder (1.25 g). The second active fractions eluted with the same solvent were collected, evaporated in vacuo, and charged on a column of reversed phase silica gel (YMC-GEL ODS-A, 2.2 id×15 cm). Elution was performed with 40% aqueous $CH_3CN$, and the active fractions were combined and concentrated to yield a semi-pure solid of BU-4726G-B (61 mg). This solid was finally purified by reverse phase preparative HPLC (column: YMC-D-ODS-5, I.D. 20×50 millimeters (mm), YMC Co. Ltd.; mobile phase: 70% MeOH in 0.067 M phosphate buffer, pH 3.5; flow rate: 10 ml/minute; detection: UV 254 nanometers (nm) to afford active eluate which was concentrated and extracted with EtOAc yielding a homogeneous yellow solid of BU-4726G-B (25 mg).

EXAMPLE 4

Physico-Chemical Properties

Physico-chemical properties of BU-4726G-A and BU-4726G-B are summarized in Table 5. Both compounds are readily soluble in chloroform, EtOAc, MeOH, acetone and dimethyl sulfoxide, but practically insoluble in benzene, n-hexane and water. They gave positive responses to iodine vapor, ferric chloride, ammonium molybdate-sulfuric acid, but negative responses to ninhydrin, Ehrich and anthrone reagents.

Figure 7:
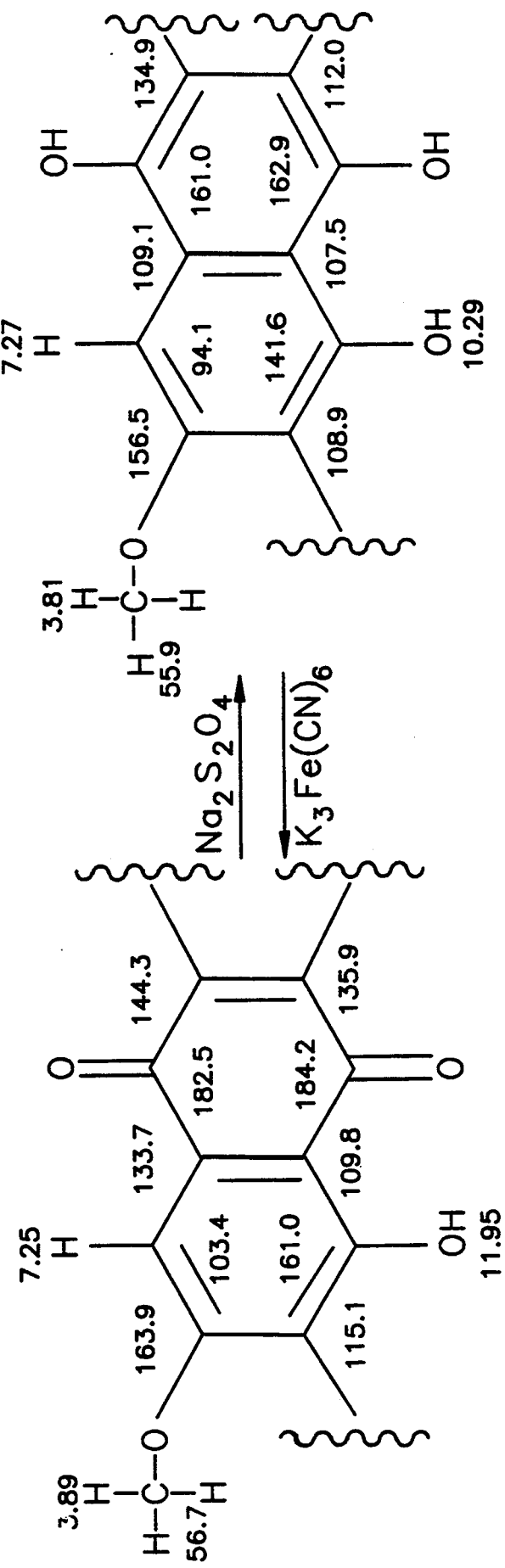
FIG. 7—The chromophores of compounds BU-4726G-A and BU-4726G-B.

BU-4726G-A showed characteristic UV absorption maxima at 236 and 445 nm in neutral and acidic MeOH which irreversibly changed to 222 and 303 nm upon alkylisation. On the other hand, BU-4726G-B showed absorption maxima at 279 and 426 nm. The molecular formulae of BU-4726G-A and BU-4726G-B were determined to be $C_{52}H_{50}O_{20}$ and $C_{52}H_{54}O_{20}$, respectively. The IR, $^1$H-NMR and $^{13}$C-NMR spectra of BU-4726G-A and BU-4726G-B are shown in FIGS. 1, 2, 3, 4, 5 and 6.

type chromophore of BU-4726G-A was changed to the hydroquinone form in BU-4726G-B. The difference of the molecular formulae between BU-4726G-A and BU-4726G-B supported these results. Extensive 2D NMR spectra analyses provided the chromophore structures of BU-4726G-A and BU-4726G-B as shown in FIG. 7.

Analytical Instruments Used

TLC was performed on precoated silica gel plates (Kieselgel 60F$_{254}$). Melting points (MP's) were determined with a Yanagimoto micro melting point apparatus and are not corrected. IR spectra were recorded on a Jasco IR-810 and UV spectra on a UVIDEC-610C spectrometer. $^1$H and $^{13}$C NMR spectra were measured on a Jeol JNM-GX 400 spectrometer operated in Fourier transform mode. FAB-MS and HRFAB-MS were obtained on a Jeol JMS-AX 505H using m-nitrobenzyl alcohol as the matrix. Optical rotations were determined with a Jasco model DIP 140.

TABLE 5

Physico-chemical Properties of BU-4726G-A and B

| | BU-4726G-A | BU-4726G-B |
|---|---|---|
| Nature | Orange amorphous powder | Yellow amorphous powder |
| Melting point | >200° C. (decomp.) | >200° C. (decomp.) |
| $[\alpha]_D$ | 160° ± 10° (c 0.5, MeOH) | −39° ± 5° (c 0.25, MeOH) |
| Molecular formula | $C_{52}H_{50}O_{20}$ | $C_{52}H_{54}O_{20}$ |
| FAB-MS (m/z) | 995(M + H)$^+$ | 999(M + H)$^+$ |
| HRFAB-MS | Found m/z 995.2990 | Found m/z 999.3294 |
| | Calcd for $C_{52}H_{51}O_{20}$ 995.2973 | Calcd for $C_{52}H_{55}O_{20}$ 999.3286 |
| Elemental Analysis | | |
| | Calcd for $C_{52}H_{50}O_{20} \cdot H_2O$ : C 61.66, H 5.17 | Calcd for $C_{52}H_{54}O_{20} \cdot H_2O$ : C 61.41, H 5.55 |
| | Found: C 61.42, H 5.10 | Found: C 61.35, H 5.27 |
| UV $\lambda_{max}$nm(E ) | | |
| MeOH | 205(398), 236(524), 278$^{sh}$(346), 445(83) | 208(473), 227$^{sh}$(495) 241(510), 279(707), 426(304) |
| IR$\nu^{KBr}_{max}$cm$^{-1}$ | 3450, 2980, 1780, 1760, 1700, 1670, 1640, 1320 | 3400, 2980, 1740, 1630 1400, 1330 |
| HPLC*(Rt min) | 3.93 | 15.27 |

*YMC packed ODS, A301-3; MeOH-0.15% phosphate buffer, 65:35, 1.0 ml/min.
UV 254 nm The $^1$H and $^{13}$C-NMR spectra of BU-4726G-A (Table 6) exhibited just a half number of signals of those expected from the molecular formula suggesting that it has a dimer type structure. Its $^1$H-NMR spectrum exhibited two methyls ($\delta$1.14 d and 1.28 s), two O-methyls ($\delta$3.86 and 3.91 s), and nine protons ($\delta$1.7 - 3.8) which are assignable to methylenes and/or methines, two aromatic protons ($\delta$5.45s and 7.25 s) and one D$_2$O exchangeable proton ($\delta$11.95 s). The $^{13}$C-NMR spectrum demonstrated 26 carbon signals including two methyl, two O-methyl, four methylene, one methine, three quaternary, two —CH=, seven >C= and five carbonyl carbons ($\delta$171.8, 179.5, 182.5, 184.2 and 193.1).

Acetylation of BU-4726G-A with acetic anhydride in pyridine afforded a tetraacetyl derivative. (m/z 1166(M+4H)$^+$). This result indicated that BU-4726G-A possessed four hydroxyl groups in its molecule. Reductive acetylation of BU-4726G-A in the presence of zinc dust gave octaacetyl derivative (m/z 1335 (M+H$^+$)) suggesting that two quinone groups are present.

BU-4726G-B is gradually converted to BU-4726G-A by air oxidation. This conversion proceeded quantitatively by the treatment of oxidizing agent such as potassium ferricyanide and also reversed by the addition of reductant such as sodium hydrosulfite. Thus, both compounds are completely interchangeable by chemical reactions. Treatment of BU-4726G-B with acetic anhydride in pyridine gave octaacetyl BU-4726G-B which is the same compound as reductive acetylation product of BU-4726G-A. These data revealed that the quinone

TABLE 6

$^{13}$C and $^1$H NMR Data of BU-4726G-A and BU-4726G-B

| BU-4726G-A$^a$ | | BU-4726G-B$^b$ | |
|---|---|---|---|
| $^{13}$C | $^1$H | $^{13}$C | $^1$H |
| 193.1(s)$^c$ | | 199.2(s) | |
| 184.2(s) | | 181.2(s) | |
| 182.5(s) | | 173.9(s) | |
| 179.5(s) | | 162.9(s) | |
| 171.8(s) | | 161.0(s) | |
| 163.9(S) | | 156.5(s) | |
| 161.0(s) | | 141.6(s) | |
| 144.3(s) | | 134.9(s) | |
| 135.9(s) | | 112.0(s) | |
| 133.7(s) | | 109.1(s) | |
| 115.1(s) | | 108.9(s) | |
| 109.8(s) | | 107.5(s) | |
| 103.4(d) | 7.25(1H,s) | 94.1(d) | 7.27(1H,s) |
| 92.1(d) | 5.45(1H,s) | 89.9(d) | 5.35(1H,s) |
| 87.6(s) | | 88.5(s) | |
| 86.4(s) | | 84.9(s) | |
| 84.5(s) | | 83.2(s) | |
| 60.5(q) | 3.91(3H,s) | 60.0(q) | 3.89(3H,s) |
| 59.4(t) | 3.68(1H,m) 3.82(1H,m) | 59.0(t) | 3.70(1H,m) 3.86(1H,m) |
| 56.7(q) | 3.89(3H,s) | 55.9(q) | 3.81(3H,s) |
| 54.5(t) | 2.70(1H,d,14.1) 3.86(1H,d,14.1) | 50.4(t) | 2.79(1H,d,18.4) 3.69(1H,d,18.4) |
| 47.5(t) | 1.92(1H,m) 2.10(1H,m) | 47.9(t) | 1.93(1H,m) 2.06(1H,m) |
| 44.9(d) | 2.58(1H,m) | 45.7(d) | 2.58(1H,m) |
| 43.1(t) | 1.74(1H,m) 1.85(1H,m) | 43.3(t) | 1.74(1H,m) 1.93(1H,m) |
| 25.5(q) | 1.28(3H,s) | 25.7(q) | 1.30(3H,s) |

TABLE 6-continued

13C and 1H NMR Data of BU-4726G-A and BU-4726G-B

| BU-4726G-A[a] | | BU-4726G-B[b] | |
|---|---|---|---|
| 13C | 1H | 13C | 1H |
| 16.1(q) | 1.14(3H,d,6.8) | 15.3(q) | 0.98(3H,d,6.9) |
| | 11.95(1H,s) | | 10.29(1H,d,0.9) |

[a]Chemical shift in ppm (solvent, CDCl3)
[b]Chemical shift in ppm (solvent, CDCl3 + CD3OD, 10:1)
[c]Multiplicity

EXAMPLE 5

Biological Properties

Antimicrobial Activity

The minimum inhibitory concentrations (MICs) of BU-4726G-A and BU-4726G-B were determined against various bacteria and fungi by the serial two-fold agar dilution method. Nutrient agar medium (Eiken) was used for bacteria and Sabouraud dextrose agar medium (Difco) for fungi. As shown in Table 7, BU-4726G-A and BU-4726G-B showed good inhibitory activity against Gram-positive bacteria, but they were much less active or inactive against the Gram-negative bacteria and fungi tested.

Antitumor Activity

BU-4726G-A and BU-4726G-B were tested for in vitro cytotoxicity against murine and human tumor cells using mitomycin C as a reference. B16-F10 (murine melanoma) and HCT-116 (human colon carcinoma) cells were grown by the method described in the previous paper (Sugawara, et al., "Eponemycin, A New Antibiotic Active Against B16 Melanoma. I. Production, Isolation, Structure, And Biological Activity," J. Antibiotics (1990) 43, 8–18). The cytotoxicity against these tumor cell lines were determined colorimetrically at 540 nm after staining viable cells with neutral red. The results were summarized in Table 8. BU-4726G-A and BU-4726G-B showed strong cytotoxicity against B16 murine melanoma cells but moderate cytotoxicity against HCT-116 cells.

TABLE 7

Antibacterial Activities of BU-4726G A and B

| | MIC (μg/ml) | | | |
|---|---|---|---|---|
| Test Organisms | BU-4726G-A | BU-4726G-B | Cefaclor | Amikacin |
| Staphylococcus aureus 209P | 6.3 | 6.3 | 0.8 | 0.4 |
| Staphylococcus aureus Smith | 12.5 | 12.5 | 0.4 | 1.6 |
| Staphylococcus aureus A15036(MRSA) | 12.5 | 12.5 | 25 | 3.1 |
| Staphylococcus epidermidis 11-1168 | 12.5 | 12.5 | 6.3 | 50 |
| Streptococcus faecalis A2808 | 12.5 | 12.5 | 25 | 50 |
| Micrococcus luteus ATCC 9341 | 3.1 | 3.1 | <0.05 | 3.1 |
| Bacillus subtilis ATCC 6633 | 3.1 | 3.1 | <0.05 | 0.4 |
| Escherichia coli K12 | >100 | >100 | 0.4 | 0.8 |
| Escherichia coli Juhl | >100 | >100 | 0.4 | 3.1 |
| Klebsiella pneumoniae PCI 602 | 100 | >100 | 0.2 | 0.4 |
| Salmonella typhi 901 | 100 | >100 | 0.2 | 3.1 |
| Pseudomonas aeruginosa A9843 A | >100 | >100 | >100 | 3.1 |

Medium: Nutrient agar (Eiken, pH 7.0)
Inoculum size: 10^5 cells/ml
Inoculated conditions: 32° C., 20 hours

TABLE 8

In vitro Cytotoxicity

| | IC50 (μg/ml) | | |
|---|---|---|---|
| Test cell | BU-4726G-A | BU-4726G-B | Mitomycin C |
| Mouse melanoma B16-F10[*1] | 0.7 | 2.2 | 1.0 |
| Human colon carcinoma HCT-116[*2] | 3.9 | 5.0 | 0.05 |

Medium
[*1]Eagle's minimum essential medium + 10% FCS
[*2]McCoy's 5A medium + 10% FCS

ATP-Sensitive K+ ($K_{ATP}$) Channel Blocking

Methods

3H-Glibenclamide binding assay was performed according to the method of French, et al. (French, et al., "Modulation of 3H-glibenclamide Binding to Cardial and Insulinoma Membranes," Eur. J. Pharmacol. (1991) 207 23). Briefly, rat insulimona cells were suspended in 50 mM TrisHCl, pH 7.4, to be about 1 × 10^7 cells/ml and gently homogenized. The homogenate (160 μl) and 2.5 nM 3H-glibenclamide (20 μl, NEN) in the presence or absence of inhibitor (20 μl) were mixed and incubated for 2 hours at room temperature. The reaction was terminated by filtering directly onto the filter mat for the Beta-plate TM Scintillation counter (Pharmacia). Non-radiolabeled glibenclamide was used as the standard inhibitor.

Results

BU-4726G-A and BU-4726G-B were assayed for their 3H-glibenclamide binding inhibitory activities. Fifty percent inhibitory concentrations (IC50) of BU-4726G-A and BU-4726G-B were 0.66 μg/ml and 0.78 μg/ml, respectively, while IC50 of glibenclamide was 0.29 μg/ml.

Discussion

BU-4726G-A and BU-4726G-B, produced by Streptomyces exfoliatus have dimer type structures which contain a naphthoquinone and a naphthohydroquinone chromophore, respectively. BU-4726G-B was converted quantitatively to BU-4726G-A by oxidizing agent such as potassium ferricyanide. Alterporriol D and E (Suemitsu, et al., "Alterporriol D and E, Modified Bianthraquinones from Alternaria porri Ciferri," Agric. Biol. Chem. (1989) 53(5), 1301–1304), crisamicin A (Nelson, et al., " Crisamicin A, a New Antibiotic From Micromonospora I. Taxonomy of the Producing Strain, Fermentation, Isolation, Physico-chemical Characterization and Antimicrobial Properties," J. Antibiotics (1986) 39, 335–344, and Ling, et al., "Isolation and Structure Determination of Crisamicin A, A New Antibiotic From *Micromonospora purpureochromogenes* subsp. halotolerans", *J. Antibiotics* (1986) 39, 345–353), and julimycin B-II (Shoji et al., "Julymycin B-II A New Antibiotic. Isolation and Characterization," *J. Antibiotics*, (1964) A17, 156–160), were reported to have dimer type structures containing naphthoquinones. The UV spectrum of BU-4726G-B is similar to that of antibiotic AB-113 (Tanaka, et al., "Antibiotic AB-113 and its Production," *Japan Kokai* (1982) 57-16825). However, the physico-chemical properties of these antibiotics are significantly different from those of BU-4726G-A and BU-4726G-B.

BU-4726G-A and BU-4726G-B showed potent inhibitory activity against Gram-positive bacteria, cytotoxicity against tumor cells, and $K_{ATP}$ channel blocking activity.

We claim:

1. Compound BU-4726G-A having the following characteristics:

(1) readily soluble in chloroform, ethyl acetate, methanol, acetone and dimethyl sulfoxide; essentially insoluble in benzene, n-hexane, and water, (2) characteristic UV absorption maxima (UV $\lambda_{max}$nm(E)) at 236 nm (524) and 445 nm (83) in neutral and acidic methanol, (3) a molecular formula of $C_{52}H_{50}O_{20}$, (4) a dimer type structure containing a naphthoquinone chromophore, (5) molecular weight as determined by mass spectroscopy (FAB-MS (m/z)) of 995 $(M+H)^+$, (6) an optical rotation ($[\alpha]_D$) of $160 \pm 10°$ (concentration 0.5%, methanol), (7) infrared spectrum having absorption bands occurring at the following frequencies (IR $\nu^{KBr}_{max}$cm$^{-1}$): 3450, 2980, 1780, 1760, 1700, 1670, 1640, and 1320, (8) positive responses to iodine vapor, ferric chloride, ammonium molybdate-sulfuric acid; negative responses to ninhydrin, Ehrlich and anthrone reagents, (9) melting point of greater than 200° C. (decomposition), and

(10) elemental analysis:
   Calculated for $C_{52}H_{50}O_{20} \cdot H_2O$:C;
   61.66, H; 5.17,
   Found: C; 61.42, H; 5.10.

2. Compound BU-4726G-B having the following characteristics:

(1) readily soluble in chloroform, ethyl acetate, methanol, acetone and dimethyl sulfoxide; essentially insoluble in benzene, n-hexane, and water, (2) characteristic UV absorption maxima (UV $\lambda_{max}$nm(E)) at 279 nm (707) and 426 nm (304) in neutral and acidic methanol, (3) a molecular formula of $C_{52}H_{54}O_{20}$, (4) a dimer type structure containing a naphthohydroquinone chromophore, (5) molecular weight as determined by mass spectroscopy (FAB-MS (m/z)) of 999 $(M+H)^+$, (6) an optical rotation ($[\alpha]_D$) of $-39° \pm 5°$ (concentration 0.25%, methanol), (7) infrared spectrum having absorption bands occurring at the following frequencies (IR $\nu^{KBr}_{max}$ cm$^{-1}$): 3400, 2980, 1740, 1630, 1400, and 1330, (8) positive responses to iodine vapor, ferric chloride, ammonium molybdate-sulfuric acid; negative responses to ninhydrin, Ehrlich and anthrone reagents, (9) melting point of greater than 200° C. (decomposition), and

(10) elemental analysis:
   Calculated for $C_{52}H_{54}O_{20} \cdot H_2O$:C;
   61.41, H; 5.55.
   Found: C; 61.35, H; 5.27.

3. A pharmaceutical composition comprising an effective amount of an active compound selected from the group consisting of compound BU4726G-A as defined in claim 1, compound BU4726G-B as defined in claim 2, and a mixture thereof, together with a pharmaceutically acceptable carrier.

4. The composition of claim 3 wherein the amount of said active compound is about 25 to about 100 weight percent of said composition.

5. A process for producing an active compound selected from the group consisting of BU4726G-A as defined in claim 1, compound BU4726G-B as defined in claim 2, or a mixture thereof comprising cultivating under aerobic conditions *Streptomyces exfoliatus* AA4510 or a mutant or variant thereof in a suitable culture medium containing a carbon source and a nitrogen source at a pH and temperature and for a time sufficient for production of said active ingredient.

6. The process of claim 5 performed at a pH of about 6 to about 8, a temperature of about 16° C. to about 48° C., for about 2 to about 10 days.

7. The process of claim 5 performed at a pH of about 7, a temperature of about 21° C. to about 37° C., for about 3 to about 5 days.

* * * * *